(12) United States Patent
Ashmead et al.

(10) Patent No.: US 9,952,139 B2
(45) Date of Patent: Apr. 24, 2018

(54) PATH LENGTH CALIBRATION SYSTEM AND METHOD

(71) Applicant: THERMO ELECTRON SCIENTIFIC INSTRUMENTS LLC, Madison, WI (US)

(72) Inventors: Damian W. Ashmead, Middletown, DE (US); James V. Howard, Madison, WI (US); Kevin K. Kim, Madison, WI (US); Andrew Martin Braasch, Fitchburg, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 53 days.

(21) Appl. No.: 15/262,171

(22) Filed: Sep. 12, 2016

(65) Prior Publication Data

US 2017/0082533 A1    Mar. 23, 2017

Related U.S. Application Data

(60) Provisional application No. 62/220,536, filed on Sep. 18, 2015, provisional application No. 62/306,793, filed on Mar. 11, 2016.

(51) Int. Cl.
  *G01N 21/01*    (2006.01)
  *G01N 21/03*    (2006.01)
  (Continued)

(52) U.S. Cl.
  CPC ......... *G01N 21/0303* (2013.01); *G01N 21/27* (2013.01); *G01N 21/31* (2013.01);
  (Continued)

(58) Field of Classification Search
  CPC .... G01N 21/0303; G01N 21/27; G01N 21/31; G01N 2021/025; G01N 2021/036;
  (Continued)

(56) References Cited

U.S. PATENT DOCUMENTS 6,628,382 B2    9/2003    Robertson
7,088,095 B1    8/2006    Busch
(Continued)

FOREIGN PATENT DOCUMENTS

EP    2166313 B1    11/2011

*Primary Examiner* — Hina F Ayub
(74) *Attorney, Agent, or Firm* — William R. McCarthy, III

(57) ABSTRACT

An apparatus includes a first pedestal surface coupled to i) a swing arm and to ii) a light source. The apparatus further includes a magnet, a base plate, a mechanical stop coupled to the base plate, and a second pedestal surface mechanically coupled to said base plate and configured to receive a liquid sample, said second pedestal surface being coupled to a spectrometer. The apparatus further includes a magnetic flux sensor located between north and south magnetic flux fields of the magnet such that the magnetic flux reaching the sensor while the mechanical stop is in physical contact with the swing arm provides a linear range of output of the magnetic flux sensor, and a processor adapted to calibrate the point for minimum optical path length using a threshold magnetic flux field emitted from the magnet and detected by the magnetic flux sensor.

20 Claims, 19 Drawing Sheets

(51) Int. Cl.
  *G01N 21/27*   (2006.01)
  *G01R 33/07*   (2006.01)
  *G01R 33/09*   (2006.01)
  *G01N 21/31*   (2006.01)
  *G01D 5/14*    (2006.01)

(52) U.S. Cl.
  CPC ........... *G01R 33/07* (2013.01); *G01R 33/093* (2013.01); *G01D 5/145* (2013.01); *G01N 2021/035* (2013.01); *G01N 2021/036* (2013.01); *G01N 2201/0668* (2013.01); *G01N 2201/08* (2013.01)

(58) Field of Classification Search
  CPC ....... G01N 2201/0668; G01N 2201/08; G01R 33/07; G01R 33/093; G01D 5/145
  USPC ....................................... 356/244
  See application file for complete search history.

(56) References Cited

U.S. PATENT DOCUMENTS

| | | |
|---|---|---|
| 8,223,338 B2 | 7/2012 | Robertson, Jr. et al. |
| 2006/0049826 A1 | 3/2006 | Daneman et al. |
| 2010/0085571 A1* | 4/2010 | Robertson, Jr. .... G01N 21/0303 356/432 |
| 2014/0008539 A1 | 1/2014 | Coffin et al. |

\* cited by examiner

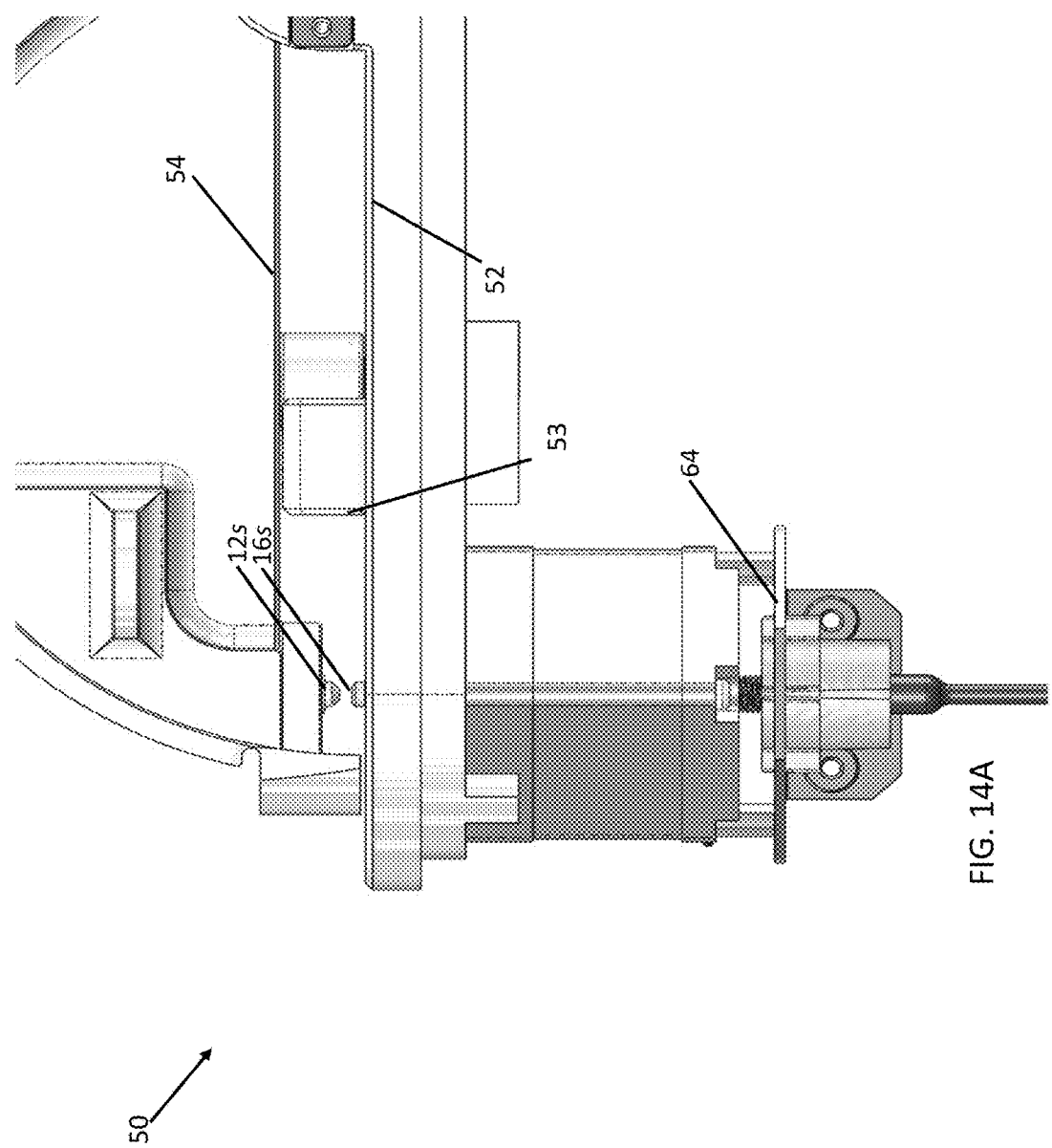

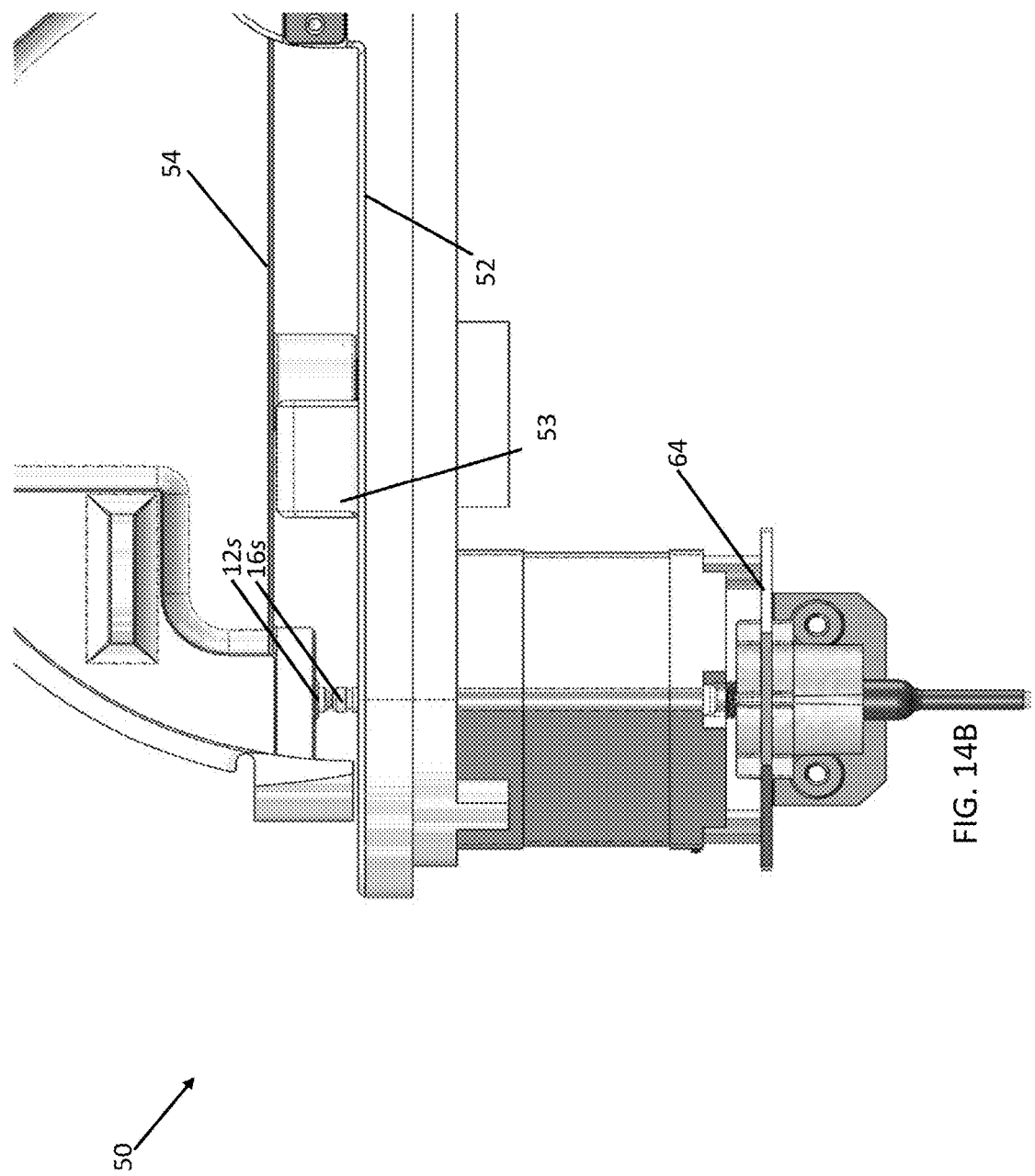

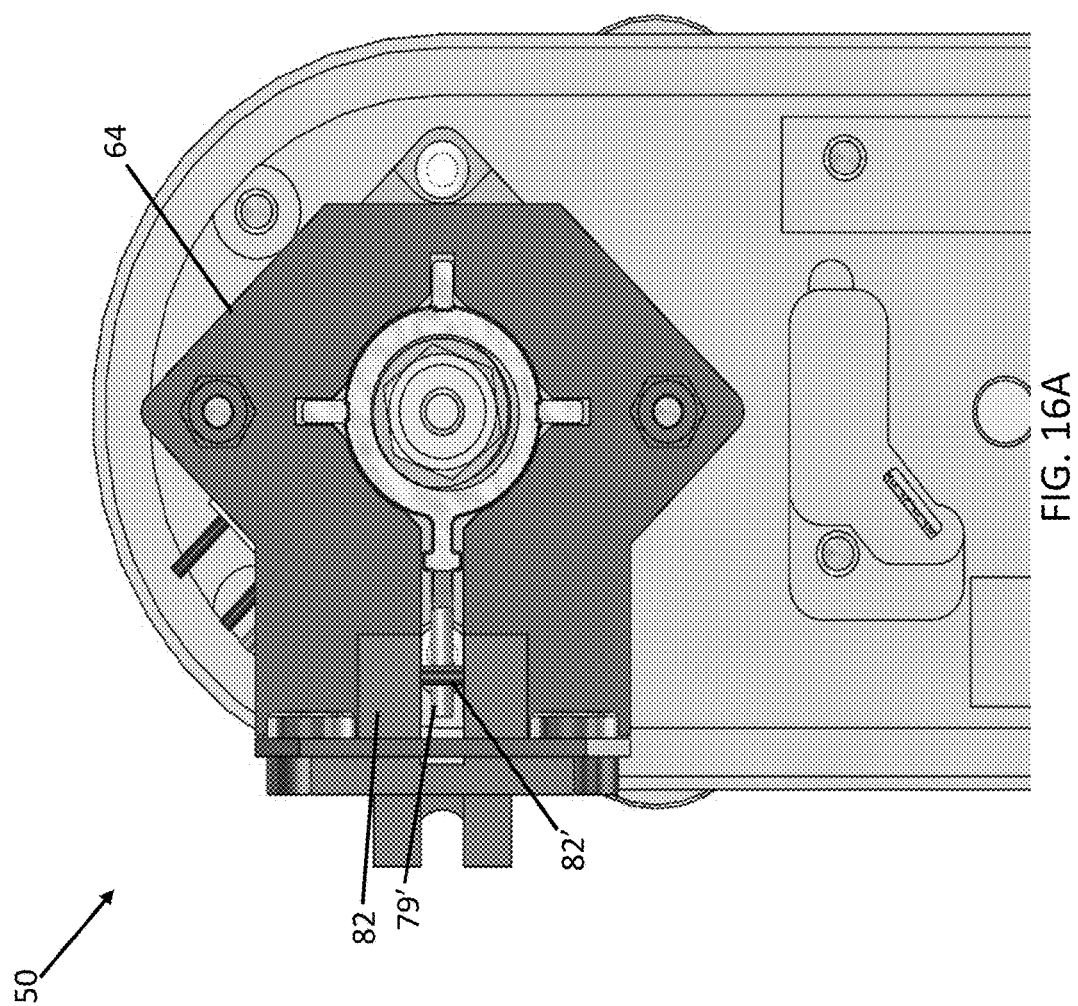

PATH LENGTH CALIBRATION SYSTEM AND METHOD

CROSS-REFERENCE TO RELATED APPLICATIONS

This application claims priority to U.S. provisional patent applications Ser. Nos. 62/220,536, filed Sep. 18, 2015 and 62/306,793, filed Mar. 11, 2016, entitled PATH LENGTH CALIBRATION SYSTEM AND METHOD, which are incorporated herein by reference in their entireties.

FIELD OF THE INVENTION

The invention is generally related to path length calibration for an apparatus for measuring an optical property of a sample.

BACKGROUND

Liquids, mixtures, solutions and reacting mixtures are often characterized using optical techniques such as spectrophotometry. In order to characterize samples of these liquids, the liquid is usually contained in a vessel referred to as a cell or cuvette, two or more of whose sides are of optical quality and permit the passage of those wavelengths needed to characterize the liquid contained therein. When dealing with very small sample volumes of, for example, from 1 to 2 microliters, it is difficult to create cells or cuvettes small enough to be filled and permit the industry standard 1 cm optical path to be used. It is also difficult and/or time consuming to clean these cells or cuvettes for use with another sample.

As shown in FIG. 1, micro-volume UV/Vis spectrophotometers described, for example, in U.S. Pat. No. 6,628,382 B2 issued to Robertson on Sep. 30, 2003, the disclosure of which is hereby incorporated by reference in its entirety (however, where anything in the incorporated reference contradicts anything stated in the present application, the present application prevails), measure the absorbance of microliter amounts of liquid samples via a sample retention technology which enables containing a liquid sample by its surface tension between surfaces 2 and 7. The liquid sample forms a column 9 between a light receiving sample interface 7 typically coupled to a first optical conduit such as an optical fiber 11, and a light transmitting sample interface 2, which is typically coupled to a second optical conduit such as an optical fiber 6. The upper 2 and lower 7 sample interfaces can be moved in relation to one another to create multiple known path lengths that are typically less than or equal to 1 mm, thereby expanding the dynamic range of the spectrophotometer for a particular sample, as described in U.S. Pat. No. 8,223,338 B2 issued to Robertson et al., on Jul. 17, 2012, the disclosure of which is hereby incorporated by reference in its entirety (however, where anything in the incorporated reference contradicts anything stated in the present application, the present application prevails). Light 3 from a light source coming through the fiber 6 contained in and flush with surface 2 (also referenced herein as the upper sample interface, or first pedestal surface) radiates downward through the liquid sample column 9 and is collected by the fiber 11 in the lower surface 7 (also referenced herein as the second pedestal surface) of the lower sample interface 4 and sent on to the analysis spectrometer for absorbance measurements.

The placement of the liquid sample is achieved by the user manually pipetting a sample (typically a microliter or two) directly onto the lower sample interface. The absorbance of the sample is measured by taking the negative log of the ratio of the amount of light ($I_0$) transmitted through the system in the absence of the sample and the amount of light (I) transmitted through the system when the sample is present in the sampling interface. Under normal conditions, the amount of light transmitted through the system when the sample is present in the sampling interface is directly proportional to the path length and the concentration of the sample, in accordance with the Beer-Lambert law.

As the use of micro-volume spectrophotometers expands and new applications arise, the need to accurately measure sample absorbance at shorter path lengths to accommodate samples with higher light absorbance properties is increasing. Presently available micro-volume UV/Vis spectrophotometers (e.g., NanoDrop™, Thermo Electron Scientific Instruments, Madison Wis.) can establish an absolute measurement path length that is accurate to approximately ±20 µm. Samples with higher light absorbance properties, however, can require measuring absorbance at path lengths as short as 30 µm.

Therefore, there is a need for an improved path length calibration system and method.

SUMMARY

In one embodiment, an apparatus for measuring an optical property of a sample includes a first pedestal surface coupled to i) a swing arm and to ii) a light source. The apparatus further includes a magnet, a base plate, a mechanical stop coupled to the base plate, and a second pedestal surface mechanically coupled to said base plate and configured to receive a liquid sample. The second pedestal surface is coupled to a spectrometer, wherein said second pedestal surface is further operable so as to adjust a separation between the first and the second pedestal surfaces at a variable distance (P) to pull the liquid sample into a column so as to be contained by surface tension, or to squeeze the sample during optical analysis, thereby providing an optical path for photometric or spectrometric measurement. The apparatus further includes a magnetic flux sensor located between north and south magnetic flux fields of the magnet such that the magnetic flux reaching the sensor while the mechanical stop is in physical contact with the swing arm provides a range of output of the magnetic flux sensor, such as a linear range of output of the magnetic flux sensor. The apparatus also includes a processor adapted to calibrate the point for minimum optical path length by utilizing a threshold magnetic flux field emitted from the magnet and detected by the magnetic flux sensor. In some embodiments, the apparatus further includes a first optical conduit coupled to the first pedestal surface. In certain embodiments, the apparatus further includes a second optical conduit coupled to the second pedestal surface. The apparatus can further include a bracket configured to permit translational movement of said second optical conduit parallel to a longitudinal axis of said second optical conduit. The magnetic flux sensor can be, for example, a linear Hall effect sensor or a giant magnetoresistive (GMR) sensor. In some embodiments, the magnetic flux sensor can be located such that a null plane of north and south magnetic flux fields of the magnet is centered on the magnetic flux sensor while the mechanical stop is in physical contact with the swing arm.

In certain embodiments, the first optical conduit includes a transmitting end and the second optical conduit includes a receiving end, with said transmitting end of said first optical conduit and said receiving end of said second optical conduit providing the optical path for photometric or spectrometric measurement. In certain other embodiments, the first optical conduit includes a receiving end and the second optical conduit includes a transmitting end, with said receiving end of said first optical conduit and said transmitting end of said second optical conduit providing the optical path for photometric or spectrometric measurement.

In some embodiments, the magnet is coupled to the swing arm, and the magnetic flux sensor is coupled to the base plate. In some other embodiments, the magnetic flux sensor is coupled to the swing arm, and the magnet is coupled to the base plate.

In certain embodiments, the bracket can further include a position sensor that provides feedback so as to enable precision displacement between said first and said second pedestal surfaces so as to enable said variable distance (P). In these specific embodiments, the position sensor can further establish a reference position when a translation control system initializes upon startup or upon being interrupted by an opto-interrupter device coupled to said second optical conduit.

In some embodiments, the apparatus can measure absorbances in a range of between about 0.005 Absorbance Units and about 2.0 Absorbance Units for any given optical path length. The first and second optical conduits can include at least one optical fiber selected from: a single-mode fiber, a polarization maintaining fiber, and a multi-mode fiber. The light source can be configured to provide optical wavelengths in a range of between about 190 nm and about 850 nm.

In another embodiment, a method of measuring an optical property of a sample includes coupling a first pedestal surface and a magnet to a swing arm and to a light source, and coupling a mechanical stop and a magnetic flux sensor to a base plate. The method further includes coupling a second pedestal surface to said base plate, the second pedestal surface configured to receive a liquid sample and further operable so as to adjust a separation between said first and said second pedestal surfaces at a variable distance (P) to pull said liquid sample into a column so as to be contained by surface tension, or to squeeze the sample during optical analysis, thereby providing an optical path for photometric or spectrometric measurement. The method also includes locating the magnetic flux sensor between north and south magnetic flux fields of the magnet such that the magnetic flux reaching the sensor while the mechanical stop is in physical contact with the swing arm provides a linear range of output of the magnetic flux sensor, and utilizing a threshold magnetic flux field emitted from the magnet and detected by the magnetic flux sensor to calibrate the point for minimum optical path length. The magnetic flux sensor and its location are as described above.

This invention has many advantages, such as enabling more accurate measurements of sample absorbance at shorter path lengths to accommodate samples with higher light absorbance properties.

BRIEF DESCRIPTION OF THE DRAWINGS

FIGS. 14A-14B are illustrations of the range of displacement of the lower optical fiber connector, from maximum (FIG. 14A) to minimum (FIG. 14B).

FIGS. 16A-16B are bottom plan views of a spectrometer according to the invention showing of the range of displacement of the opto-interrupter device, from a position above the "home" position (FIG. 16A) to the "home" position (FIG. 16B).

Like reference numerals refer to corresponding parts throughout the several views of the drawings.

DETAILED DESCRIPTION OF EMBODIMENTS

Figure 1:
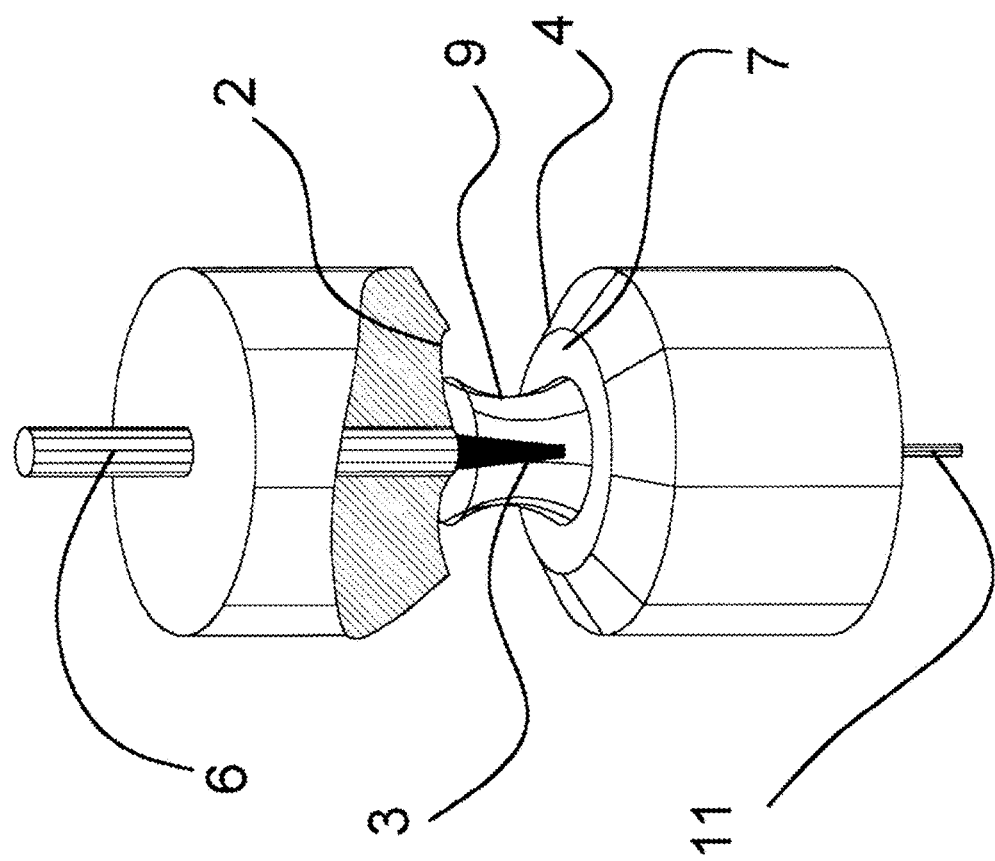
FIG. 1 is an illustration of a cutaway section of the optical path in a prior art spectrophotometer.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Figure 2:
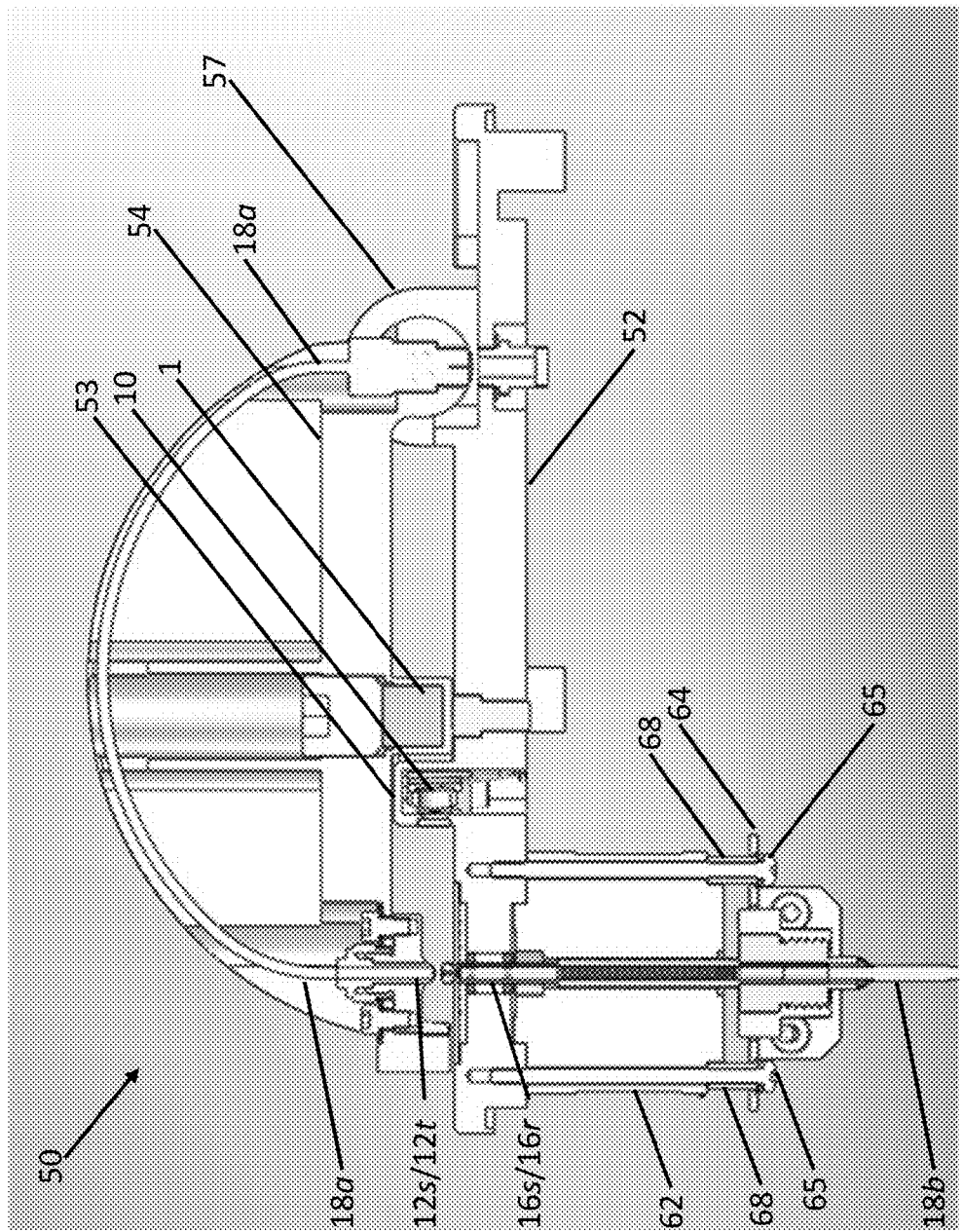
FIG. 2 is an illustration of a side view of an embodiment of a spectrophotometer according to the invention shown in the "closed" position.
Figure 3:
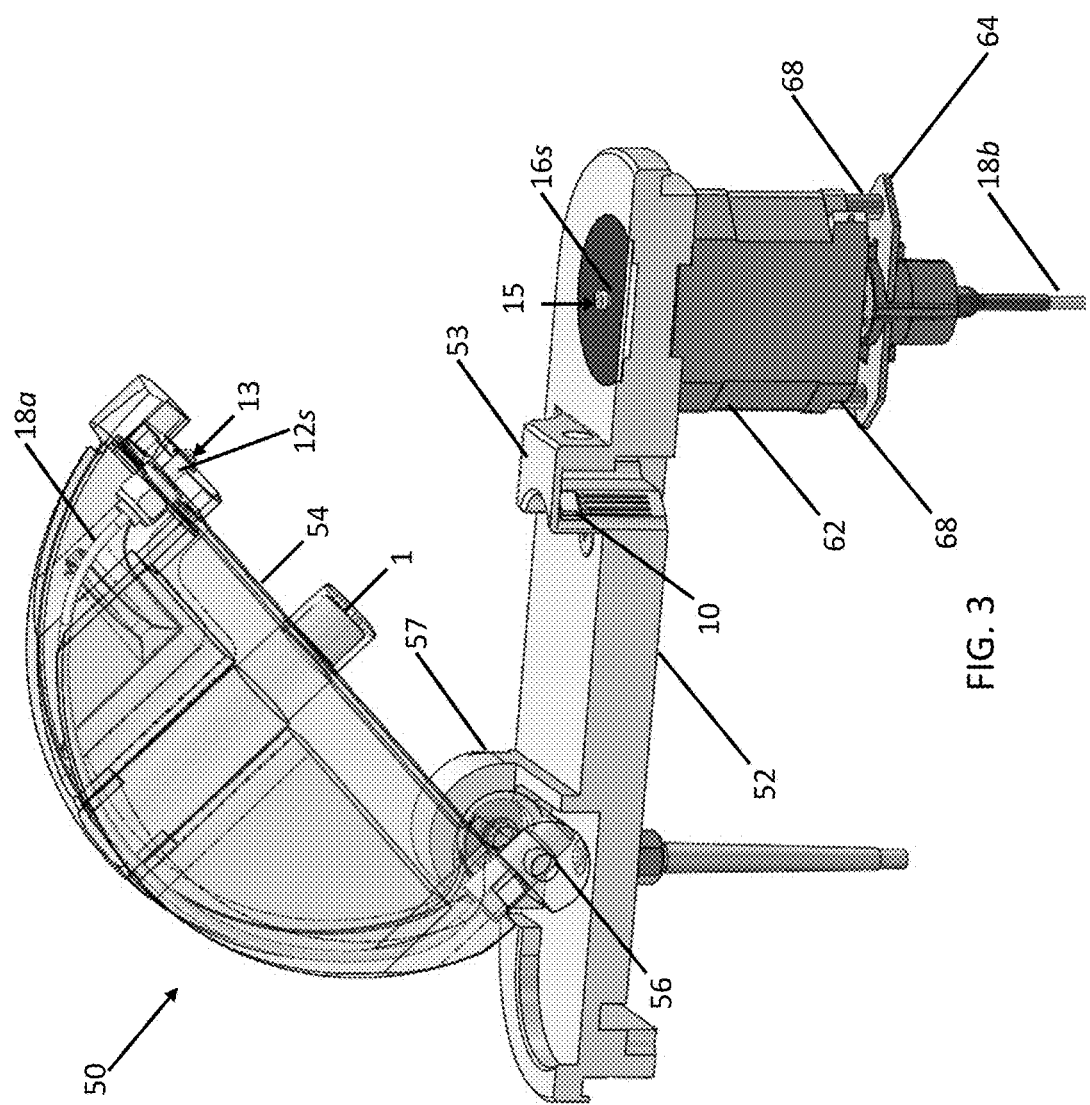
FIG. 3 is an illustration of a perspective view of an embodiment of a spectrophotometer according to the invention shown in the "open" position.

Turning now to the drawings, FIGS. 2-3 are side views of an example apparatus in accordance with an embodiment of the invention. In particular, the apparatus, as illustrated in FIG. 3 and generally designated by the reference numeral 50, is shown in an "open" position in which a liquid drop analyte or reference sample of less than about 10 µl, more often less than about 2 µl, is dispensed or aspirated onto a lower platform surface 15 (also referenced herein as the second pedestal surface). As discussed in more detail below, such an "open" position enables easy access to the ends of the surfaces, e.g., surface 15, which contain the liquid samples and also enable a user to easily clean such surfaces and to mount a new sample within the apparatus when desired.

Thus, in the "open" position of FIG. 3, the dispensing of a liquid sample of less than about 10 often less than about 2 can often be delivered by way of a pipetting means (not shown), such as, but not limited to, a Finnpipette® from Thermo Fisher Scientific of Waltham, Mass. The pipetted liquid is thus delivered to the lower platform 15, which is often configured as a pedestal or anvil-like surface that may include the end of a custom or commercial SMA fiber optic connector 16s, and of which, also may in some applications, be treated with a material known by those of ordinary skill in the art to prevent over spreading of the applied liquid drop analyte or reference sample (not shown).

Thereafter, upon the application of liquid drop, the apparatus 50, as now shown in FIG. 2, is angularly moved by a user to be in the "closed" position, so as to result in the upper pedestal or anvil-like surface 13 (also referenced herein as the first pedestal surface), as specifically referenced in FIG. 3, also often the end of a custom or commercial SMA fiber optic connector 12s, to be brought into contact with a dispensed liquid drop sample (not shown) to constrain a desired liquid drop sample therebetween with lower surface 15, also specifically referenced in FIG. 3, in a surface tension mode at a variable distance (p) to pull the liquid sample into a column 9 (as shown in FIG. 1) so as to be contained by surface tension, or to squeeze the sample during optical analysis, thereby providing an optical path for photometric or spectrometric measurement.

As shown by the open position of FIG. 3 resulting in the closed position of FIG. 2, such an angular movement of the swing arm 54 is enabled by the mechanical coupling of a hinge rod 56 configured therethrough bores in both the swing arm 54 and in the hinge spacer block 57, with hinge spacer block 57 being rigidly fixed with respect to base plate 52. Accordingly, the fiber optic connector 12s, which contains surface 13, and of which is mounted within and passes through a bore in swing arm 54, also angularly rotates with respect to a base plate 52 about hinge rod 56 in order to come into contact with a liquid drop sample dispensed on surface 15. A mechanical stop 53 coupled to the base plate 52 provides a desired position against which the lower surface of the arm 54 abuts when the arm is rotated so as to provide for the contact and measurement of liquid drop sample.

As also illustrated in FIGS. 2 and 3, a pair of optical conduits, such as, for example, an upper optical fiber 18a (also referenced herein as the first optical conduit) and a lower optical fiber 18b (also referenced herein as the second optical conduit) and disposed within respective connectors, e.g., connectors 12s and 16s, enable optical communication by way of being diametrically opposed with one another in their operating position, i.e., the "closed position" illustrated in FIG. 2. It is to be noted that such optical conduits, e.g., optical fibers 18a and 18b, can be of any type, such as, single-mode fibers, polarization maintaining fibers, but preferably multi-mode fibers.

Figure 12:
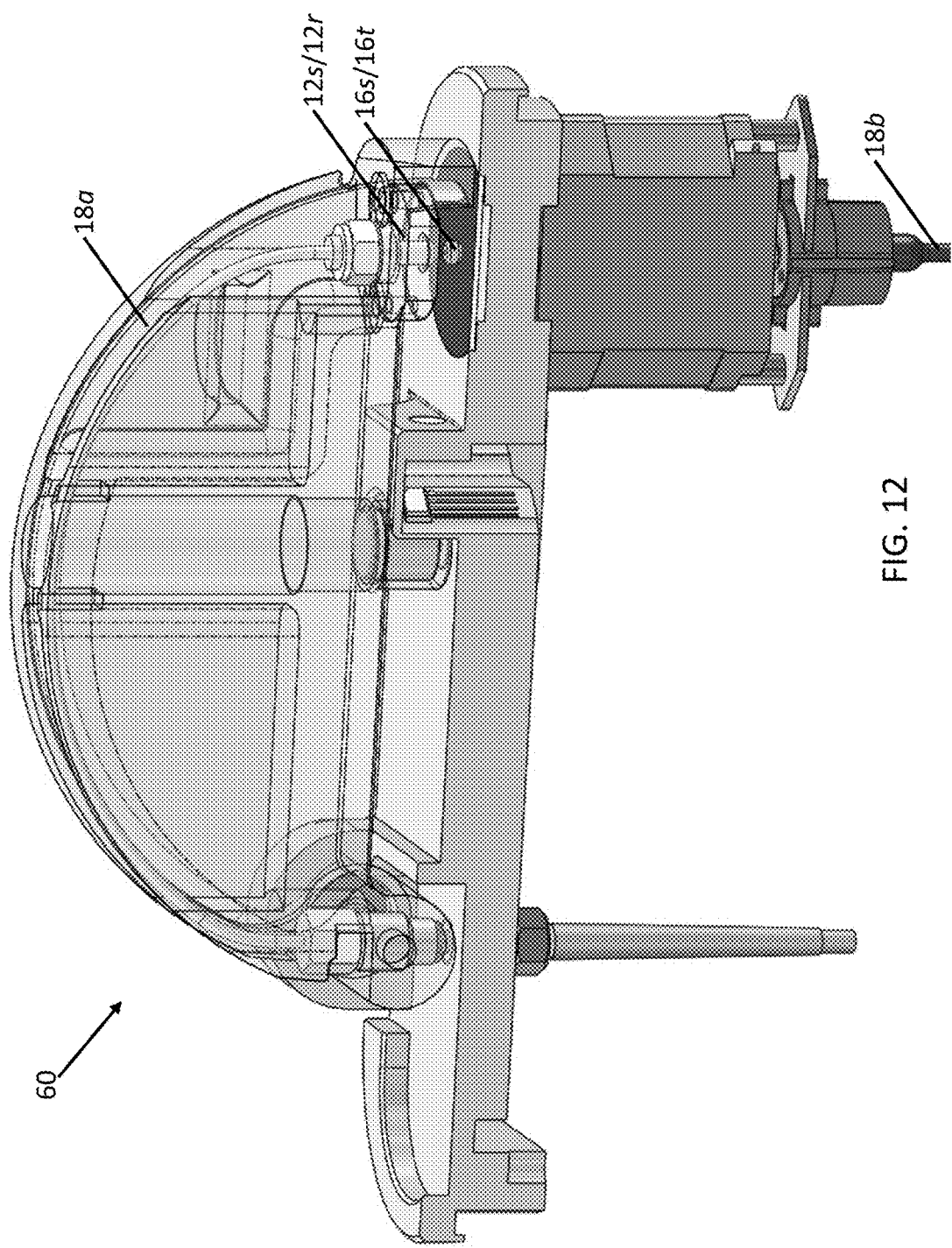
FIG. 12 is another illustration of a side view of an embodiment of a spectrophotometer according to the invention.

In certain embodiments of the apparatus 50, as shown in FIG. 2, the first optical conduit 18a is the transmitting end 12t, with or without an optical fiber forming the first optical conduit 18a, and the optical connector 16a of the second optical conduit 18b is the receiving end 16r, with or without an optical fiber forming the second optical conduit 18b, with said transmitting end 12t of said first optical conduit 18a and said receiving end 16r of said second optical conduit 18b providing the optical path for photometric or spectrometric measurement. In certain other embodiments of the apparatus 60, as shown in FIG. 12, the first optical conduit 18a is the receiving end 12r, with or without an optical fiber forming the first optical conduit 18a, and the optical connector 16s of the second optical conduit 18b is the transmitting end 16t, with or without an optical fiber forming the second optical conduit 18b, with said receiving end 12r of said first optical conduit 18a and said transmitting end 16t of said second optical conduit 18b providing the optical path for photometric or spectrometric measurement.

Turning now exclusively to FIG. 2 so as to describe the precise positioning of the surfaces 15 and 13 for measurement of a desired sample, it is to be noted that the lower optical fiber holder 16s for the lower optical fiber 18b also serves as a shaft for a linear actuator, as described in greater detail below. Although the upper optical fiber connector 12s (and consequently the coupled optical conduit fiber 18a) is fixed with respect to the swing arm 54, the lower optical fiber connector 16s (and consequently the lower optical conduit, e.g., fiber 18b) may translate, parallel to its axis (e.g., along the vertical direction), so as to enable the spacing between the two optical fibers to be varied. The range of displacement of the lower optical fiber connector 16s from the maximum to the minimum optical spacing between the two optical fibers is shown in FIGS. 14A and 14B, respectively. The base plate 52 is provided with a linear actuator that is mounted thereto so as provide for the precise translation of the lower optical fiber connector 16s. As shown in FIG. 2, the linear actuator may include a motor 62 that is secured to the base plate 52 by means of fasteners 65 (such as, for instance, screws, posts, pins, rivets, etc. with or without associated bushings). The fasteners may also include extended motor mounting screws and may pass through bushings 68 which provide a slidable mechanical engagement with a plate or bracket 64, as further described below.

As generally illustrated in FIG. 2, the motor is designed to produce a rotational motion of a threaded nut (not shown) which bears on a mating threaded shaft portion (not shown) of the lower optical fiber holder 16s. The lower fiber optic connector 16s replaces and/or serves as the actuator shaft of the linear actuator. The rotation of the internally threaded screw against the externally threaded shaft portion, as driven in either direction by the motor 62, causes controlled translation of the lower fiber optic connector 16s and the disposed optical conduit, e.g., 18b housed therein. The position of the lower fiber optic connector 16s is stabilized by a plate or bracket 64 which is mechanically coupled to the motor 62. The plate or bracket 64 may have holes or slots (not shown) through which the bushings 68 and the fasteners, such as screws 65, pass. The fasteners 65 may comprise extended motor mounting screws. The motor 62 may be further secured to the base plate 52 by additional fasteners (not shown).

As a beneficial arrangement, the motor 62 may be a commercially available motor or linear actuator or linear translator motor. As but one example, a linear actuator motor assembly is available from Haydon Switch Instruments of Waterbury Conn. USA as part no. 28H43-05-036. The actuator shaft of a standard off-the-shelf linear actuator or linear translator apparatus may need to be replaced by the lower fiber optic holder 16s, as described herein.

Figure 4:
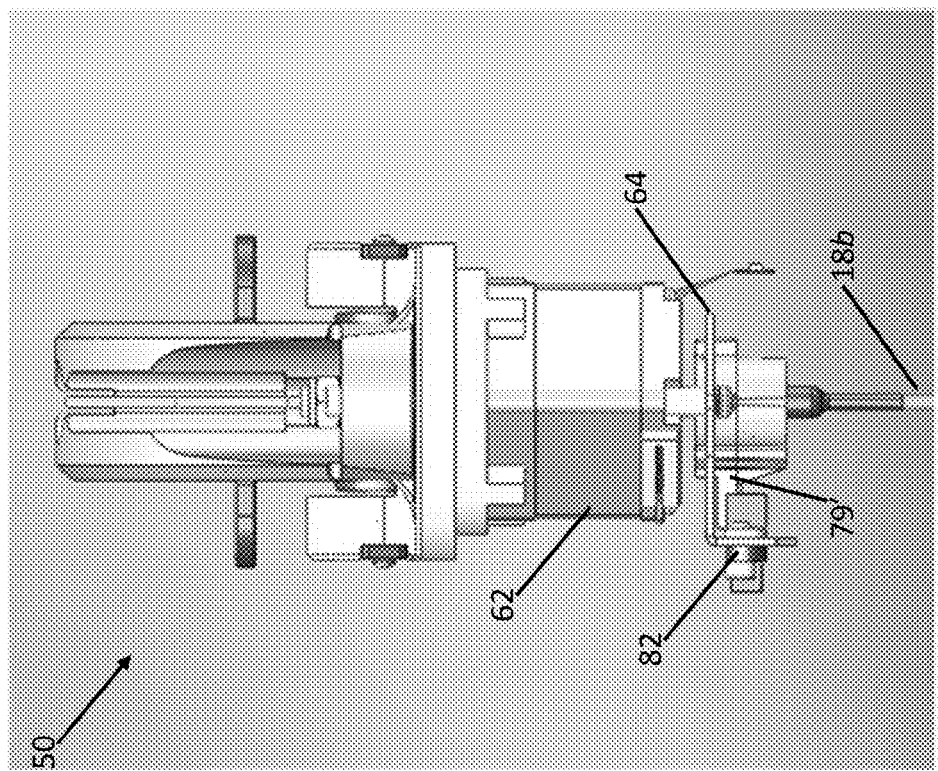
FIG. 4 is an illustration of a rear view of an embodiment of a spectrophotometer according to the invention shown in the "closed" position.

As shown in FIG. 4, a position sensor 82 and opto-interrupter device 79' (also referenced herein as a "home flag") coupled to the second optical conduit 18b, which are used to establish a "home" position, are located beneath the lower pedestal surface where the optical path length is established and a measurement is made. The opto-interrupter device 79' is mechanically coupled to the lower optical fiber holder 16s (shown in FIG. 3) and translates linearly through the bracket 64. The displacement range of the opto-interrupter device 79' is shown in FIGS. 15A-B, and 16A-B, from a position above the "home" position, shown in FIGS. 15A and 16A, to the "home" position shown in FIGS. 15B and 16B, where the LED beam 82' of the position sensor 82 is interrupted by the opto-interrupter device 79'. While the accuracy and repeatability of the sensor is approximately ±5 μm, experimentation and analysis has shown that the resulting absolute path length accuracy can vary by as much as ±20 μm between the upper and lower pedestal surfaces due to wear over time and thermal expansion of the components in the mechanism. At longer path lengths, 1.00 mm-0.100 mm, this is overcome with the use of differential absorbance measurements, where the difference in absorbance of the sample measured at 2 path lengths is used to determine the true absorbance of the sample, taking advantage of the system's ability to control the relative position of the moving pedestal surface to approximately ±4 μm. In other words, while the absolute path length accuracy may be in error by as much as 20 μm from the target, the system is capable of controlling the distance moved between two path lengths to within approximately 4 μm. However, at path lengths less than 0.100 mm, the use of the differential absorbance method is not practical, as the allowable difference in the distance between path lengths becomes substantially shorter than the path lengths themselves. Likewise, as the allowable difference in the distance between path lengths decreases, even a relative positional accuracy of 4 μm becomes a substantial error.

As discussed above, as the use of micro-volume spectrophotometers in the market expands and new applications are developed, the need to increase the dynamic range of the spectrophotometer has increased. Such applications are now requiring path lengths as small as 30 μm for taking accurate photometric measurements of liquid samples. In order to overcome the absolute positioning error of the system described above, it was determined that a more appropriate reference or "home" position would be the exact position where the upper and lower pedestals first make contact, or the zero path length position. If this position can be detected accurately and perhaps more importantly, with high precision, a measurement of the path length can then be made that is much less sensitive to the effects of thermal expansion and/or component wear.

Several ways to accomplish this zero path length calibration have been disclosed in US patent publication US 2014/0008539 A1 of Coffin et al., the disclosure of which is hereby incorporated by reference in its entirety (however, where anything in the incorporated reference contradicts anything stated in the present application, the present application prevails). In one embodiment, an apparatus for measuring an optical property of a sample includes a first pedestal surface coupled to i) a swing arm and to ii) a light source, a magnet, a base plate, a mechanical stop coupled to the base plate, and a second pedestal surface mechanically coupled to said base plate and configured to receive a liquid sample. The second pedestal surface is coupled to a spectrometer, wherein said second pedestal surface is further operable so as to adjust a separation between the first and the second pedestal surfaces at a variable distance (P) to pull the liquid sample into a column so as to be contained by surface tension, or to squeeze the sample during optical analysis, thereby providing an optical path for photometric or spectrometric measurement. The apparatus further includes a magnetic flux sensor located between north and south magnetic flux fields of the magnet such that the magnetic flux reaching the sensor while the mechanical stop is in physical contact with the swing arm provides a linear range of output of the magnetic flux sensor. The apparatus also includes a processor adapted to calibrate the point for minimum optical path length by utilizing a threshold magnetic flux field emitted from the magnet and detected by the magnetic flux sensor. The apparatus can further include a first optical conduit coupled to the first pedestal surface, a second optical conduit coupled to the second pedestal surface, and, optionally, a bracket configured to permit translational movement of said second optical conduit parallel to a longitudinal axis of said second optical conduit. In one improved apparatus 50 for detecting the contact position of the upper 13 and lower 15 pedestals, as shown in FIGS. 2-3, a linear Hall effect sensor 10 is fixed to the base plate 52 and a magnet 1 is fixed to the swing arm 54. The magnet 1 is positioned such that the null plane of its north and south magnet flux fields is relatively centered on the linear Hall effect sensor 10. The linear Hall effect sensor 10 is positioned to detect a change in the magnetic flux field emitted from the magnet 1 as the swing arm 54 is lifted by the lower pedestal 15 first making contact with the upper pedestal 13. Post processing of the linear Hall effect sensor 10 readout is then used to establish an accurate position corresponding to zero path length. Alternative magnetic sensors to detect a change in the magnetic flux emitted from the magnet 1 include giant magnetoresistive (GMR) sensors that output a change in resistance in response to a change in magnetic flux field.

Figure 13:
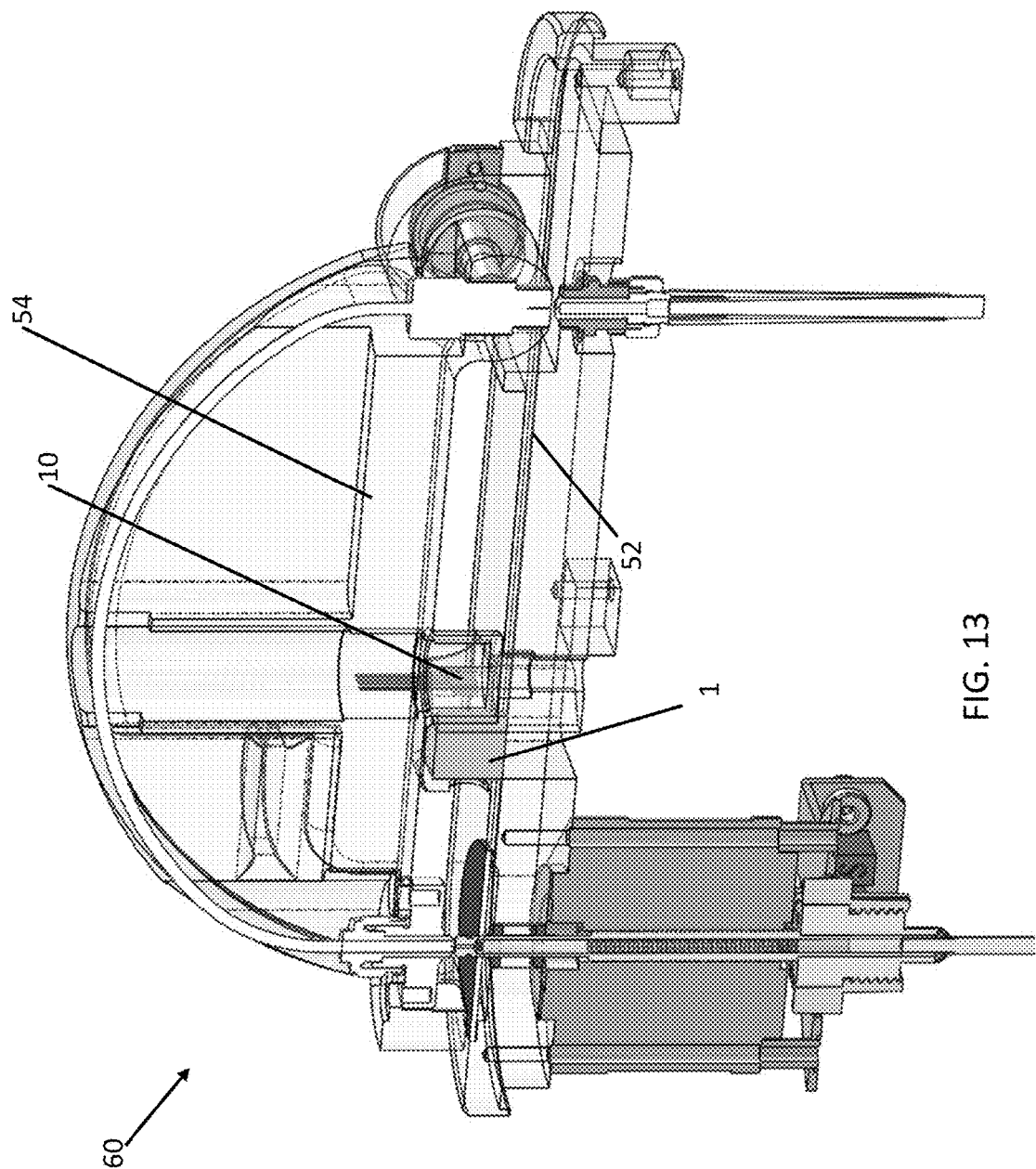
FIG. 13 is another schematic illustration of a side view of an embodiment of a spectrophotometer according to the invention.
Figure 15A:
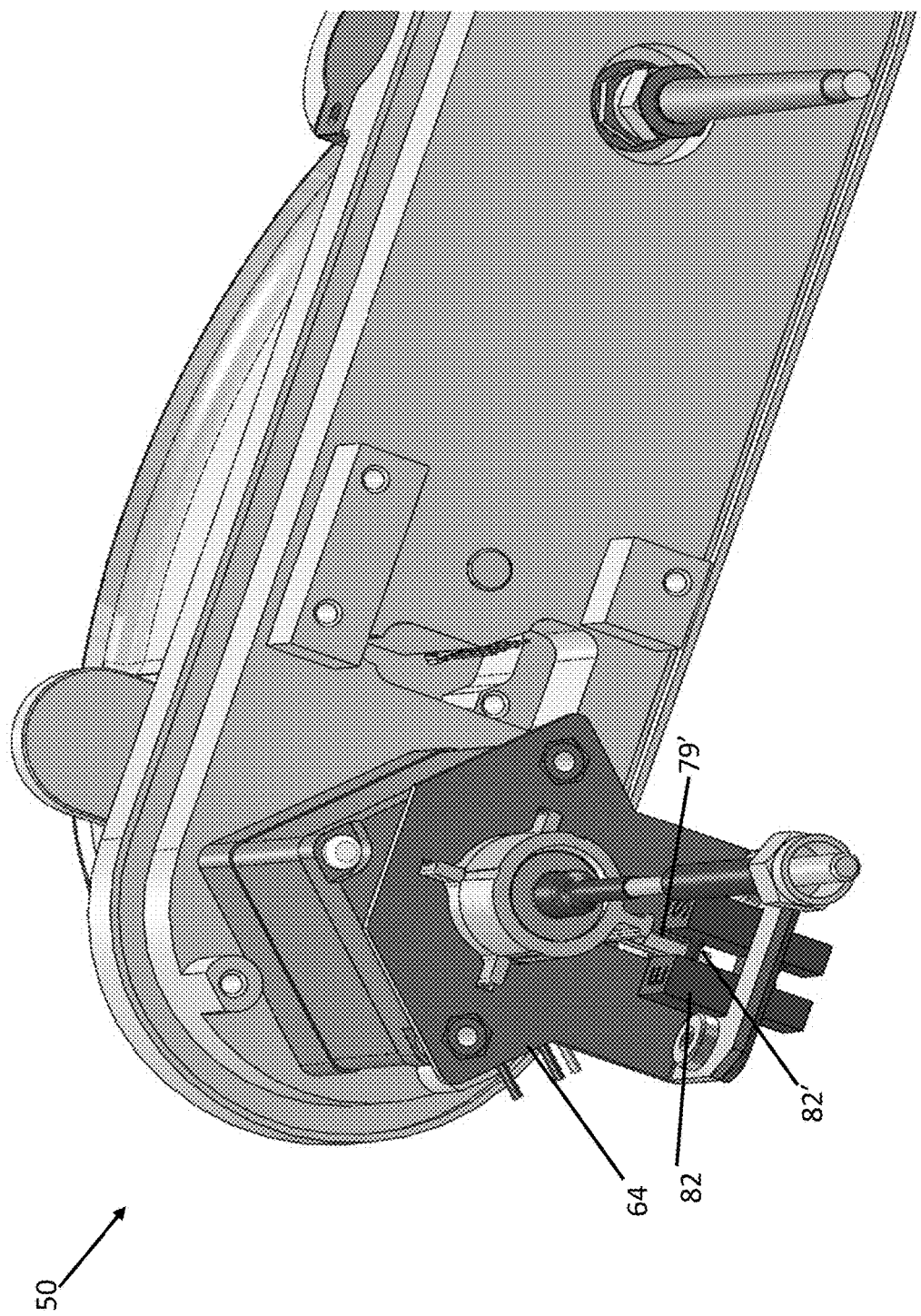
FIGS. 15A-15B are perspective bottom views of a spectrometer according to the invention showing of the range of displacement of the opto-interrupter device, from a position above the "home" position (FIG. 15A) to the "home" position (FIG. 15B).
Figure 15B:
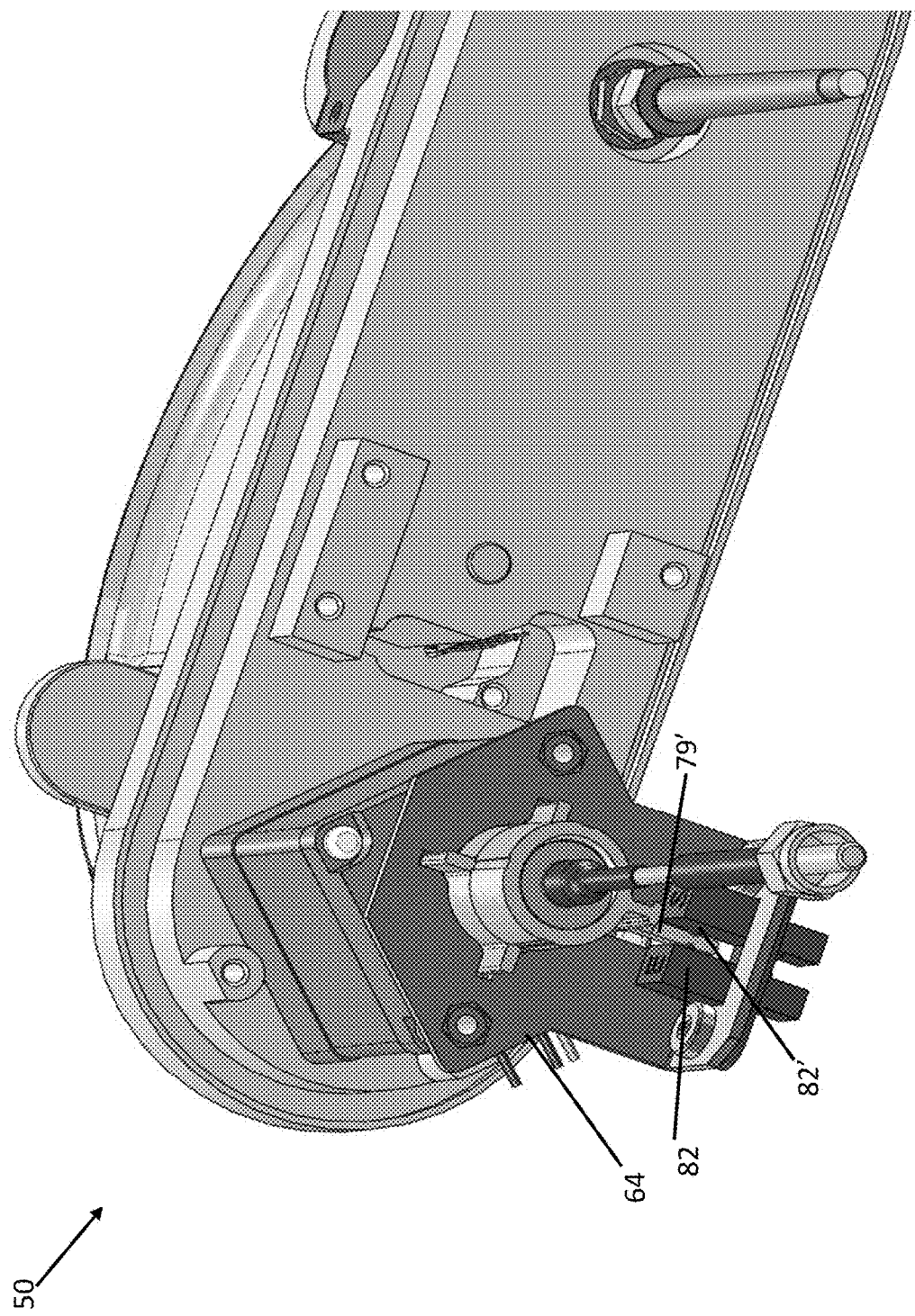
Figure 16B:
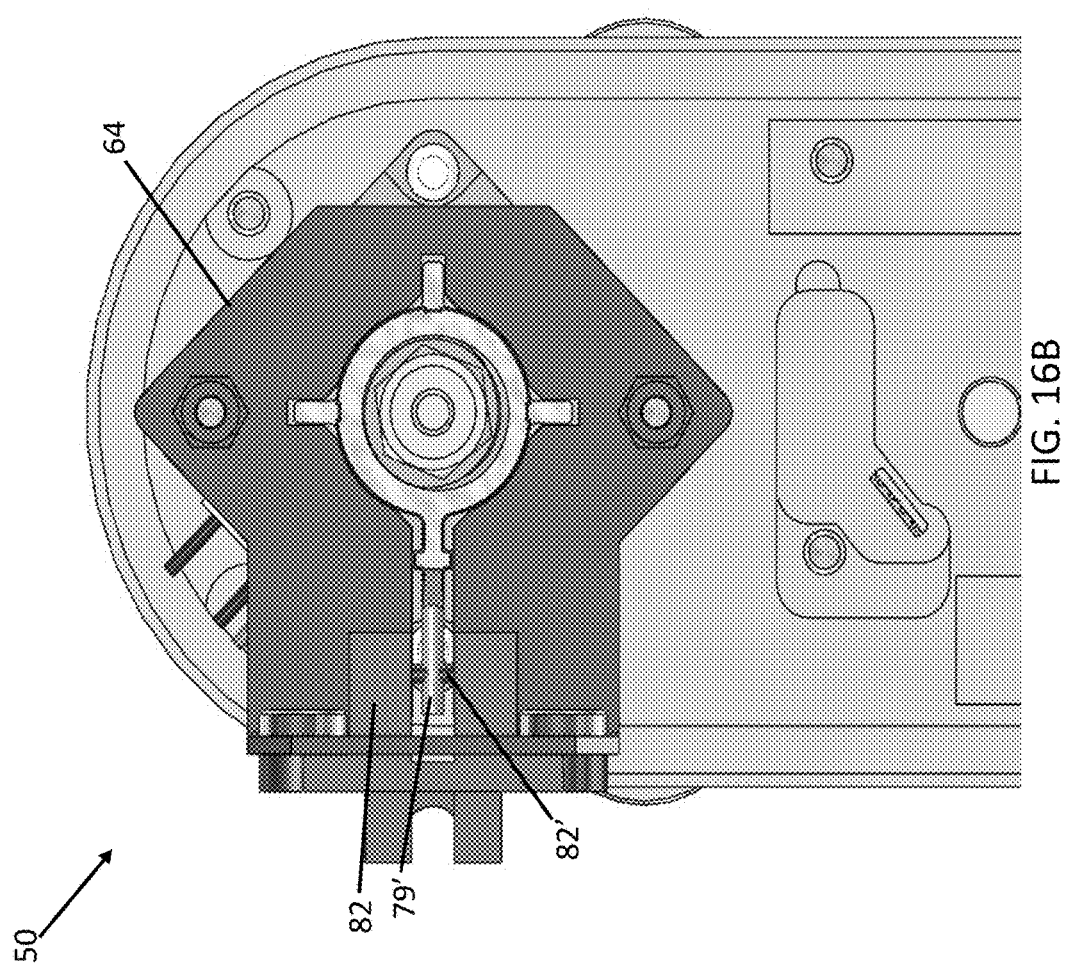

In another embodiment of the apparatus 60, as shown in FIG. 13, the linear Hall effect sensor 10 is coupled to the swing arm 54, and the magnet 1 is coupled to the base plate 52.

Figure 5:
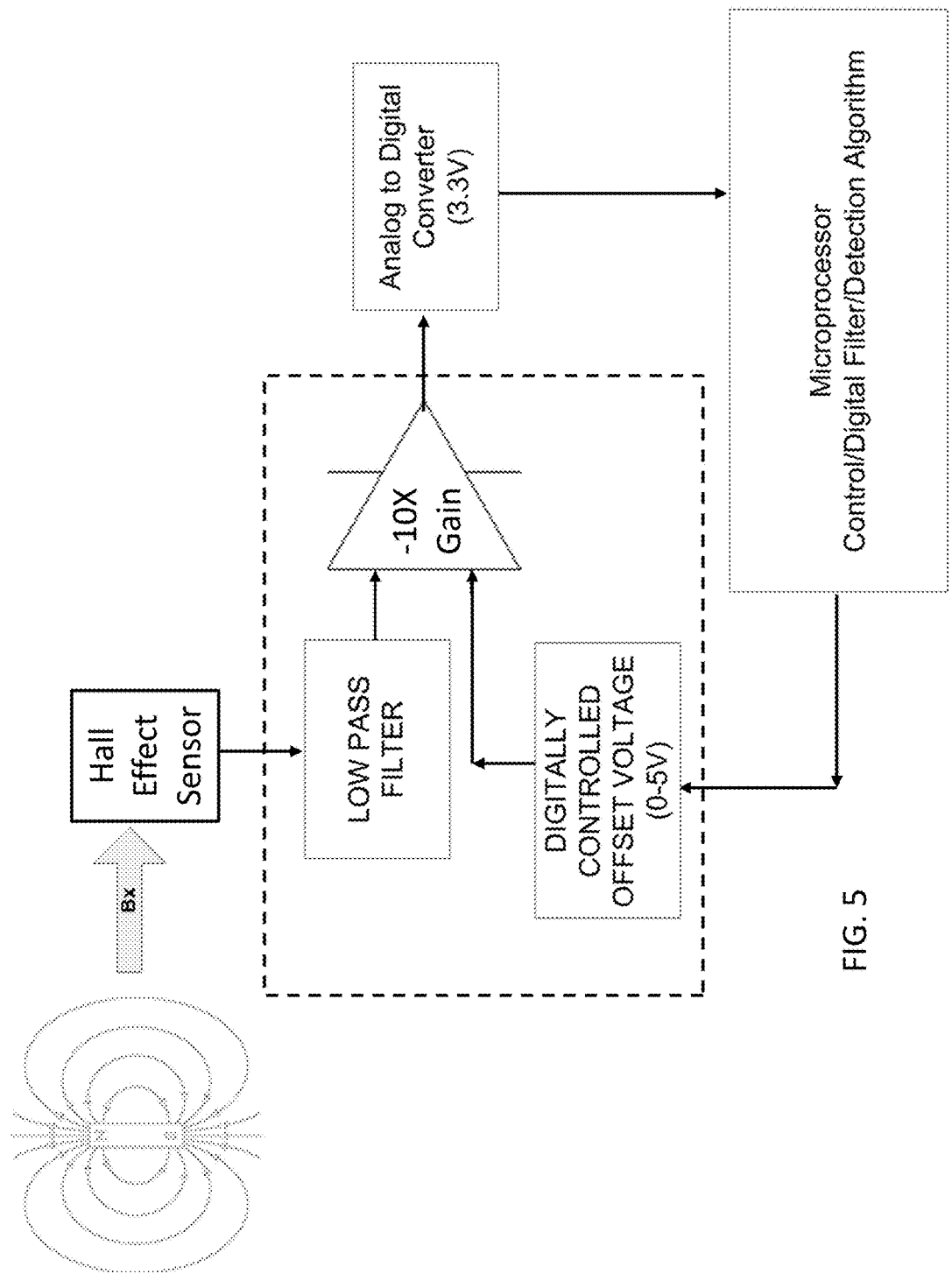
FIG. 5 is a schematic illustration of signal processing of the linear Hall effect sensor readout used to establish an accurate position corresponding to zero path length.

In one embodiment, the operation of the linear Hall effect sensor 10 is shown in FIG. 5 and described in the following steps:

1) A cylindrical bar magnet 1 is installed in the swing arm 54 of the spectrophotometer 50, oriented as shown in FIG. 5, with the N pole up.

2) The location of the magnet 1 is such that with the swing arm 54 down, the midpoint of the magnet body is on the horizontal axis of the linear Hall effect sensor 10.

3) The linear Hall effect sensor 10 is located in the base plate 52 of the spectrophotometer 50. Suitable linear Hall effect sensors are available, for example, from Melexis (Melexis NV, Belgium) under part number MLX90215.

4) The linear Hall effect sensor 10 reacts only to the magnetic flux of the magnet 1 in the X direction.

5) The nominal magnetic flux in the X direction should be equal to zero with the swing arm 54 in physical contact with the mechanical stop 53 (the "down" position).

6) However, due to imperfections in magnetization of the cylindrical bar magnet 1 and positional tolerance allowances in the assembly, the actual magnetic flux reaching the linear Hall effect sensor can be non-zero. Therefore, the linear Hall effect sensor is programmed with adequate sensitivity and offset, as described below, to provide a linear range of output voltage over the expected range of static flux, that is, the magnetic flux reaching the sensor when the swing arm is down.

7) A low pass filter is applied to remove noise from the linear Hall effect sensor output. The low pass filter is optimized for noise reduction while maintaining an adequate response time for measuring the change in magnetic flux as the swing arm is moved with the stepper motor operating at 100 steps/sec.

8) The filtered signal is amplified by −10× to increase sensitivity to flux change.

Figure 6:
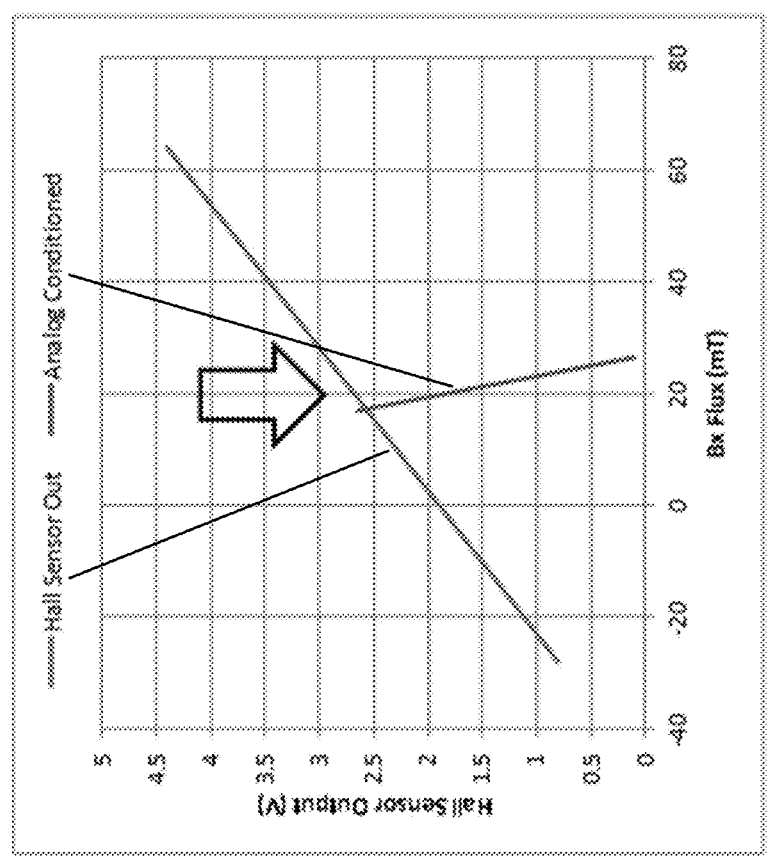
FIG. 6 is a graph of linear Hall effect sensor output (V) as a function of magnetic field flux (mT).

9) An offset voltage keeps the amplified signal within the linear range of the op-amp and analog-to-digital converter (ADC). The offset voltage is controlled by a microprocessor, and the offset is swept over the available range to find a point where the output is near the center of the ADC input range (0-3.3V). As shown in FIG. 6, the red line shows the final system transfer function (flux to voltage) after the offset is adjusted for a case where the static flux is 20 milliTesla (mT). Note that sensitivity is substantially increased for small changes in flux near the quiescent operating point.

10) The conditioned signal is then digitized by the ADC at 12 bits resolution.

11) Optionally, a digital filter and a detection algorithm are implemented on the microprocessor.

12) Resulting performance characteristics: A) approximately 5 ADC counts per micron of swing arm travel; B) variation in swing arm position when swing arm movement is detected (also referenced herein as "zero path length") is ±2 μm.

Figure 7:
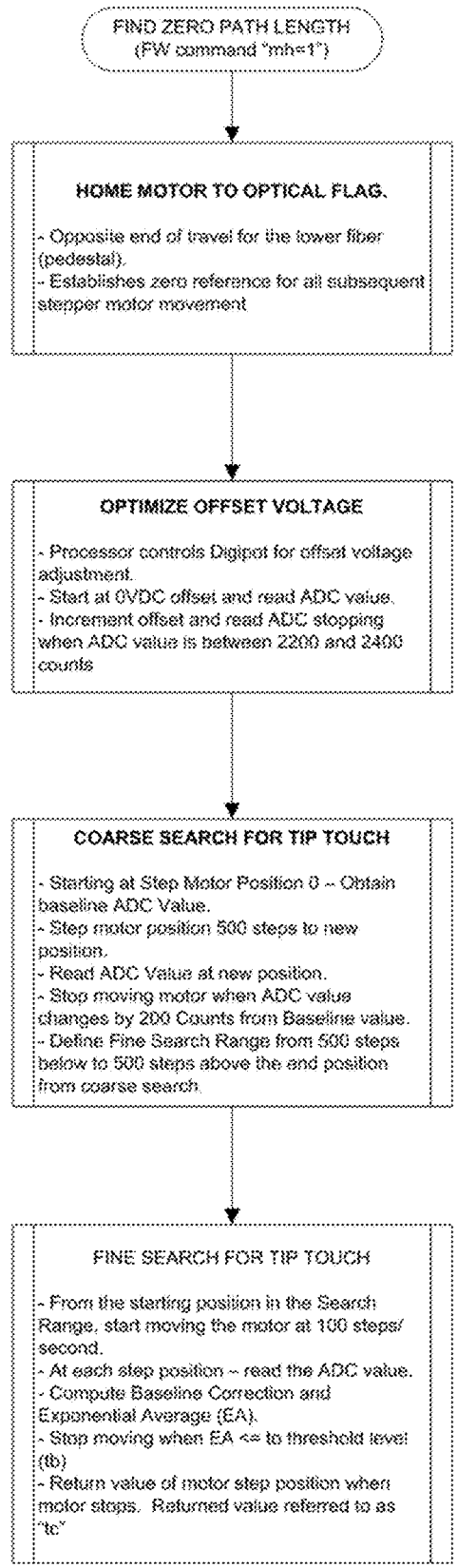
FIG. 7 is a flowchart of the method of establishing an accurate position corresponding to zero path length.
Figure 8:
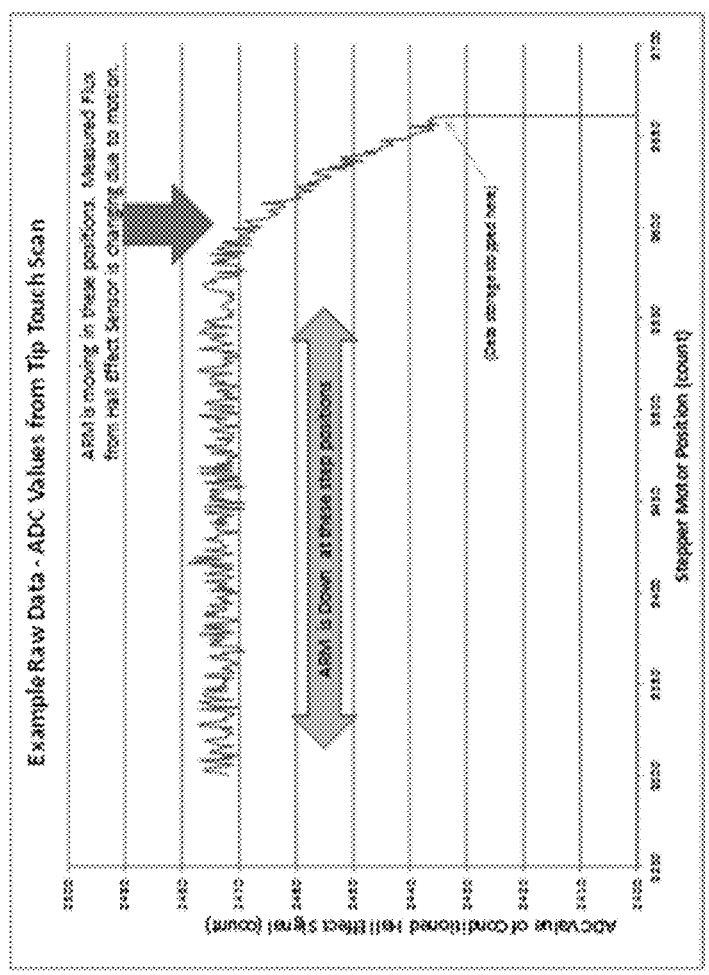
FIG. 8 is a graph of ADC value of conditioned linear Hall effect sensor signal (counts) as a function of stepper motor position (counts).
Figure 9:
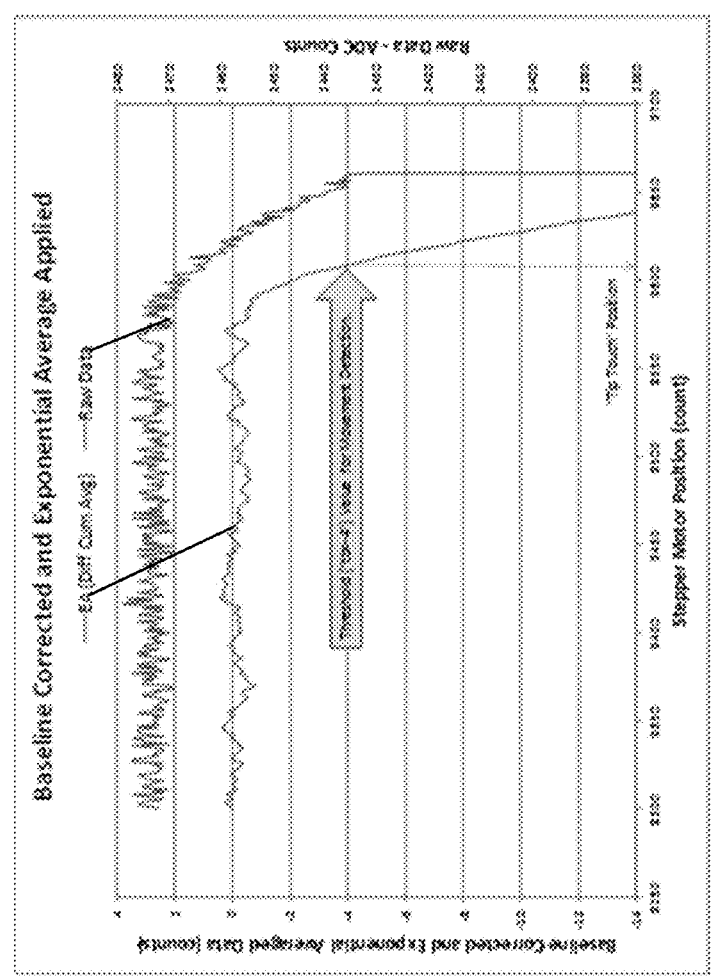
FIG. 9 is a graph of baseline corrected and exponential averaged data (counts) as a function of stepper motor position (counts).
Figure 10:
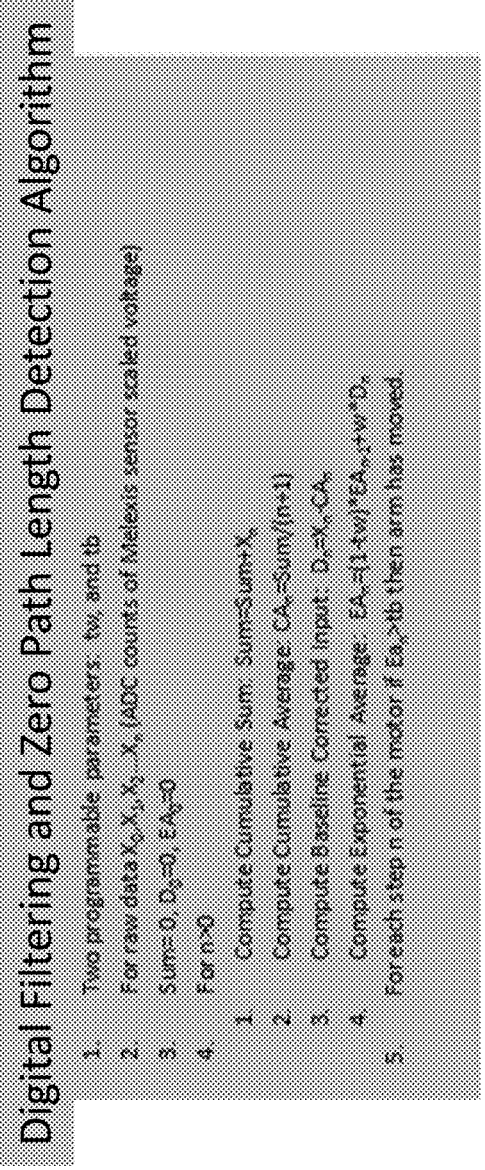
FIG. 10 is an illustration of a digital filtering and zero path length detection algorithm.

A flowchart of zero path length detection is shown in FIG. 7. An example of ADC values of conditioned linear Hall effect sensor signal and baseline corrected and exponential averaged data are shown in FIGS. 8 and 9, respectively. It is apparent from the data shown in FIGS. 8 and 9 that the swing arm moves substantially before zero path length is triggered. This movement is necessary in order for the magnetic flux to change at the location of the linear Hall effect sensor. However, this displacement is tolerable as long as the arm displacement is reasonably close to the actual point where the mechanical stop was in physical contact with the swing arm, and the displacement is repeatable. To balance these requirements, "tb" was set to equal a value of −4, that is, four counts below the exponentially averaged baseline. The absolute value of the threshold magnetic flux field corresponding to tb=−4 varies with offset adjustments. In one embodiment, the threshold magnetic flux field was equal to 0.012 mT at the linear Hall effect sensor. The exponential averaging weighing factor is 0.03 in the digital filtering and zero path length detection algorithm shown in FIG. 10. As with the electronic filter shown in FIG. 5, this digital filter coefficient was selected as a compromise between noise reduction and phase delay, while maintaining repeatability.

In one embodiment, a method of measuring an optical property of a sample includes coupling a first pedestal surface and a magnet to a swing arm and to a light source, and coupling a mechanical stop and a magnetic flux sensor to a base plate. The method further includes coupling a second pedestal surface to said base plate, the second pedestal surface configured to receive a liquid sample and further operable so as to adjust a separation between said first and said second pedestal surfaces at a variable distance (P) to pull said liquid sample into a column so as to be contained by surface tension, or to squeeze the sample during optical analysis, thereby providing an optical path for photometric or spectrometric measurement. The method also includes locating the magnetic flux sensor between north and south magnetic flux fields of the magnet such that the magnetic flux reaching the sensor while the mechanical stop is in physical contact with the swing arm provides a linear range of output of the magnetic flux sensor, and utilizing a threshold magnetic flux field emitted from the magnet and detected by the magnetic flux sensor to calibrate the point for minimum optical path length. An exemplary zero path length detection method, shown in FIG. 7, includes the following steps:

1. Move lower fiber connector 16s to the home position of optical flag 79'. (Home motor to optical flag)
   a. establishes the zero reference for all subsequent stepper motor movement
2. Optimize offset voltage
   a. offset voltage adjustment is processor controlled (Digi-pot)
   b. start at 0VDC offset and read ADC value
   c. increment offset voltage and read ADC value, stopping incrementing offset voltage when ADC value is in a range of between 2200 and 2400 counts
3. Coarse search for zero path length
   a. starting at motor step position 0, obtain baseline ADC value
   b. move motor position 500 steps to new position
   c. read ADC value at new position
   d. stop moving motor when ADC value changes by 200 counts from baseline value
   e. define fine search range from 500 steps below to 500 steps above the end motor position from coarse search
4. Fine search for zero path length
   a. from the starting position in the fine search range, start moving the motor at 100 steps/second
   b. at each step position—read the ADC value
   c. compute baseline correction and exponential average (EA)
   d. stop moving when EA≤threshold magnetic flux level (tb)
   e. return value of motor step position when motor stops. The returned value is referred to as "tc."

Figure 11:
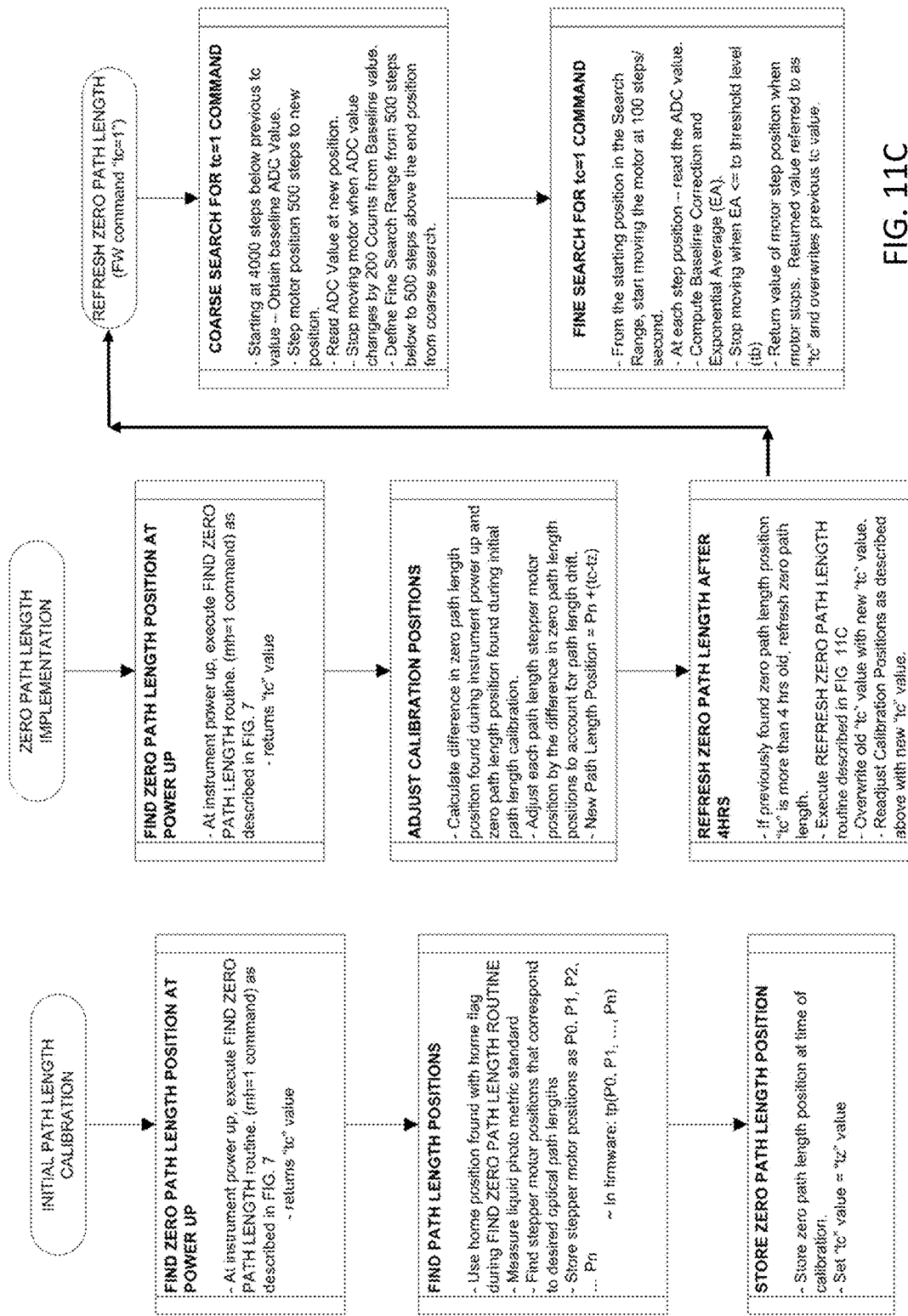
FIGS. 11A-11C are flowcharts of initial path length calibration (FIG. 11A), zero path length implementation (FIG. 11B) and zero path length refresh (FIG. 11C).

An embodiment of the path length calibration method is shown in FIGS. 11A-C. An exemplary initial path length calibration, as shown in FIG. 11A, includes the following steps:

1. Find the zero path length position at power up
   a. at instrument power up, execute Find Zero Path Length routine (mh=1 command) as described above and shown in FIG. 7.—returns "tc" value
2. Find path length positions a. use home position found with home flag during Find Zero Path Length routine b. measure a liquid known photometric standard, such as potassium dichromate, or a mixture of nicotinic acid and potassium nitrate c. find stepper motor positions that correspond to desired optical path lengths, for example, the stepper motor position at which the measured absorbance of the photometric standard is 0.740 Absorbance units (corresponding to a known path length of 1000 μm), and other multiples thereof (e.g., stepper motor positions at 0.0222, 0.037, 0.074, and 0.148 Absorbance Units)

d. store stepper motor positions as P0, P1, P2, . . . Pn—in firmware: tp(P0, P1, P2, . . . Pn)

3. Store zero path length position a. store zero path length position at time of calibration b. set "tc" value="tz" value An exemplary implementation of zero path length, as shown in FIG. 11B, includes the following steps:

1. Find zero path length position at power up a. at instrument power up, execute Find Zero Path Length routine (mh=1 command) as described above and shown in FIG. 7—returns "tc" value 2. Adjust calibration positions a. calculate difference in zero path length position found during instrument power up and zero path length position found during initial path length calibration (described above and shown in FIG. 11A)

b. adjust each path length stepper motor position by the difference in zero path length positions to account for path length drift—new path length position=Pn+(tc−tz)

3. Refresh zero path length after a determined period of time, such as 4 hours a. if the previously found zero path length position "tc" is more than 4 hours old, then b. execute a Refresh Zero Path Length routine as described below and shown in FIG. 11C c. overwrite old "tc" value with new "tc" value d. readjust calibration positions as described above with new "tc" value An exemplary refresh zero path length calibration ("tc=1 command), as shown in FIG. 11C, includes the following steps:

1. Coarse search for zero path length a. starting at 4000 steps below previous tc value—obtain baseline ADC value b. step motor position 500 steps to new position c. read ADC value at new position d. stop moving motor when ADC value changes by 200 counts from baseline value e. define Fine Search Range from 500 steps below to 500 steps above the end position from coarse search 2. Fine search for zero path length a. from the starting position in the Fine Search Range, start moving the motor at 100 steps/second b. at each step position, read the ADC value c. compute baseline correction and exponential average (EA)

d. stop moving when EA≤threshold magnetic flux level (tb)

e. return value of motor step position when motor stops. The returned value is referred to as "tc" and overwrites the previous "tc" value.

One alternative implementation method is to eliminate the use of the home flag and position sensor located below the stepper motor as a reference position and use the zero path length position discovered during a modified zero path length detection (mh=1) routine to establish a zero position. Path length calibration positions would then reference the zero path length position rather than the home position. Another alternative is to eliminate the path length calibration process, which stores discrete stepper motor positions based on a reference position for each path length of interest, and rely on the zero path length position and pitch of the lead screw to determine the number of motor steps require to achieve any desired path length.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for measuring an optical property of a sample, the apparatus comprising:
   a. a first pedestal surface coupled to i) a swing arm and to ii) a light source;
   b. a magnet;
   c. a base plate;
   d. a mechanical stop coupled to the base plate;
   e. a second pedestal surface mechanically coupled to said base plate and configured to receive a liquid sample, said second pedestal surface being coupled to a spectrometer, wherein said second pedestal surface is further operable so as to adjust a separation between said first and said second pedestal surfaces at a variable distance (P) to pull said liquid sample into a column so as to be contained by surface tension, or to squeeze the sample during optical analysis, thereby providing an optical path for photometric or spectrometric measurement;
   f. a magnetic flux sensor located between north and south magnetic flux fields of the magnet such that the magnetic flux reaching the sensor while the mechanical stop is in physical contact with the swing arm provides a linear range of output of the magnetic flux sensor; and
   g. a processor adapted to calibrate the point for minimum optical path length by utilizing a threshold magnetic flux field emitted from the magnet and detected by the magnetic flux sensor.

2. The apparatus of claim 1, wherein the first pedestal surface is coupled to a first optical conduit.

3. The apparatus of claim 2, wherein the second pedestal surface is coupled to a second optical conduit.

4. The apparatus of claim 3, wherein said first and said second optical conduits comprise at least one optical fiber selected from: a single-mode fiber, a polarization maintaining fiber, and a multi-mode fiber.

5. The apparatus of claim 3, further including a bracket configured to permit translational movement of said second optical conduit parallel to a longitudinal axis of said second optical conduit.

6. The apparatus of claim 5, wherein said bracket further comprises a position sensor that provides feedback so as to enable precision displacement between said first and said second pedestal surfaces so as to enable said variable distance (P).

7. The apparatus of claim 6, wherein said position sensor further establishes a reference position when a translation control system initializes upon startup or upon being interrupted by an opto-interrupter device coupled to said second optical conduit.

8. The apparatus of claim 3, wherein the first optical conduit includes a transmitting end and the second optical conduit includes a receiving end, with said transmitting end of said first optical conduit and said receiving end of said second optical conduit providing the optical path for photometric or spectrometric measurement.

9. The apparatus of claim 3, wherein the first optical conduit includes a receiving end and the second optical conduit includes a transmitting end, with said receiving end of said first optical conduit and said transmitting end of said second optical conduit providing the optical path for photometric or spectrometric measurement.

10. The apparatus of claim 1, wherein the magnetic flux sensor is a linear Hall effect sensor.

11. The apparatus of claim 1, wherein the magnetic flux sensor is a giant magnetoresistive (GMR) sensor.

12. The apparatus of claim 1, wherein the magnetic flux sensor is located such that a null plane of north and south magnetic flux fields of the magnet is centered on the magnetic flux sensor while the mechanical stop is in physical contact with the swing arm.

13. The apparatus of claim 1, wherein the magnet is coupled to the swing arm, and the magnetic flux sensor is coupled to the base plate.

14. The apparatus of claim 1, wherein the magnetic flux sensor is coupled to the swing arm, and the magnet is coupled to the base plate.

15. The apparatus of claim 1, wherein said apparatus measures absorbances in a range of between about 0.005 Absorbance Units and about 2.0 Absorbance Units for any given optical path length.

16. The apparatus of claim 1, wherein the light source is configured to provide optical wavelengths in a range of between about 190 nm and about 850 nm.

17. A method of measuring an optical property of a sample, the method comprising:
   a. coupling a first pedestal surface and a magnet to a swing arm and to a light source;
   b. coupling a mechanical stop and a magnetic flux sensor to a base plate;
   c. coupling a second pedestal surface to said base plate, the second pedestal surface configured to receive a liquid sample and further operable so as to adjust a separation between said first and said second pedestal surfaces at a variable distance (P) to pull said liquid sample into a column so as to be contained by surface tension, or to squeeze the sample during optical analysis, thereby providing an optical path for photometric or spectrometric measurement;
   d. locating the magnetic flux sensor between north and south magnetic flux fields of the magnet such that the magnetic flux reaching the sensor while the mechanical stop is in physical contact with the swing arm provides a linear range of output of the magnetic flux sensor; and
   e. utilizing a threshold magnetic flux field emitted from the magnet and detected by the magnetic flux sensor to calibrate the point for minimum optical path length.

18. The method of claim 17, wherein the magnetic flux sensor is located such that a null plane of north and south magnetic flux fields of the magnet is centered on the magnetic flux sensor while the mechanical stop is in physical contact with the swing arm.

19. The method of claim 17, wherein the magnetic flux sensor is a linear Hall effect sensor.

20. The method of claim 17, wherein the magnetic flux sensor is a giant magnetoresistive (GMR) sensor.

* * * * *